(12) United States Patent
Von Wolff et al.

(10) Patent No.: US 9,764,055 B2
(45) Date of Patent: Sep. 19, 2017

(54) WOUND DRESSING

(71) Applicant: BSN MEDICAL GMBH, Hamburg (DE)

(72) Inventors: Axel Von Wolff, Hamburg (DE); David Pérez-Foullerat, Madrid (ES); Marco Schubert, Hamburg (DE)

(73) Assignee: BSN MEDICAL GMBH, Hamburg (DE)

( * ) Notice: Subject to any disclaimer, the term of this patent is extended or adjusted under 35 U.S.C. 154(b) by 0 days.

(21) Appl. No.: 14/347,224

(22) PCT Filed: Sep. 26, 2012

(86) PCT No.: PCT/EP2012/068965
§ 371 (c)(1),
(2) Date: Mar. 25, 2014

(87) PCT Pub. No.: WO2013/045494
PCT Pub. Date: Apr. 4, 2013

(65) Prior Publication Data
US 2014/0236112 A1    Aug. 21, 2014

(30) Foreign Application Priority Data

Sep. 26, 2011    (EP) ...................................... 11182779

(51) Int. Cl.
*A61F 13/00* (2006.01)
*A61L 15/00* (2006.01)
(Continued)

(52) U.S. Cl.
CPC ........ *A61L 15/44* (2013.01); *A61F 13/00063* (2013.01); *A61F 13/022* (2013.01);
(Continued)

(58) Field of Classification Search
CPC .......... A61F 2013/00119; A61F 13/206; A61F 13/0213; A61F 13/022; A61F 2013/00225; A61F 2013/00702; A61F 2013/00778; A61F 2013/00782; A61F 2013/0074; A61F 2013/00744; A61F 2013/00855; A61F 2013/00097; A61F 2013/00404; A61F 2013/00761; A61F 2013/00523;
(Continued)

(56) References Cited

U.S. PATENT DOCUMENTS 4,617,326 A    10/1986    Bjornberg et al.
5,056,510 A *  10/1991    Gilman .......................... 602/52
(Continued)

FOREIGN PATENT DOCUMENTS

EP    0053936 A2    6/1982
WO    2004/060225 A1    7/2004

OTHER PUBLICATIONS

Extended European Search Report, EP11182779.6, Mar. 2, 2012.
(Continued)

*Primary Examiner* — Peter S Vasat
(74) *Attorney, Agent, or Firm* — Patterson + Sheridan, LLP

(57) ABSTRACT

The present application is concerned with an improved wound dressing for use in the treatment of skin wounds with some level of exudation, especially for use in those wounds which are infected or under risk of being infected by microorganisms.

18 Claims, 3 Drawing Sheets

(51) Int. Cl.
*A61L 15/44* (2006.01)
*A61L 15/46* (2006.01)
*A61L 15/52* (2006.01)
*A61F 13/02* (2006.01)
*A61F 13/15* (2006.01)
*A61L 15/26* (2006.01)

(52) U.S. Cl.
CPC .... *A61F 13/0209* (2013.01); *A61F 13/15577* (2013.01); *A61L 15/26* (2013.01); *A61L 15/46* (2013.01); *A61L 15/52* (2013.01); *A61F 2013/0074* (2013.01); *A61F 2013/0091* (2013.01); *A61F 2013/00748* (2013.01); *A61L 2300/404* (2013.01)

(58) Field of Classification Search
CPC .. A61F 2013/00548; A61F 2013/00604; A61F 2013/00608; A61F 13/023; A61F 13/0246; A61F 13/0279; A61F 13/0283; A61F 2013/00229; A61F 2013/00719; A61F 2013/00723; A61F 2013/0077; A61F 2013/5113; A61F 2013/51134; A61F 2013/530802; A61F 13/0226; A61F 2013/53463; A61F 13/00085; A61F 2013/00817; A61F 13/0269; A61F 2013/00302; A61F 2013/00553; A61F 2013/00561; A61F 2013/00565; A61F 2013/795; A61F 15/00; A61F 2013/00655; A61F 13/00063; A61F 13/0209; A61F 2013/00748; A61F 2013/0091; A61L 15/26; A61L 15/44; A61L 2300/404

USPC ..... 602/41–43, 46, 58; 442/22, 26; 427/2.31

See application file for complete search history.

(56) References Cited

U.S. PATENT DOCUMENTS

| | | | | |
|---|---|---|---|---|
| 5,635,201 | A | * | 6/1997 | Fabo .......................... 424/443 |
| 7,304,202 | B2 | * | 12/2007 | Sigurjonsson et al. ......... 602/58 |
| 7,576,256 | B2 | * | 8/2009 | Bjornberg et al. ............ 602/48 |
| 2008/0114279 | A1 | | 5/2008 | Becker et al. |
| 2008/0171958 | A1 | * | 7/2008 | Gundersen ..................... 602/56 |

OTHER PUBLICATIONS

International Search Report and Written Opinion, PCT/EP2012/068965, Oct. 26, 2012.

Extended European Search Report for European Application No. EP 16161424.3 dated Jun. 17, 2016.

* cited by examiner

WOUND DRESSING

FIELD OF THE INVENTION

This application relates to an improved wound dressing for use in the treatment of skin wounds with some level of exudation, especially for use in those wounds which are infected or under risk of being infected by microorganisms. The dressing comprises a treated fabric layer for contact with the wound and an absorbent core, wherein the treated fabric is not bonded or laminated to the absorbent core.

BACKGROUND

The use of water-occlusive and/or moisture-retentive dressings for treating skin wounds like pressure sores and ulcers of varied etiology is well widespread in the wound care field. These dressings are frequently a combination of a water-impervious and vapor-permeable membrane, which forms the outer surface of the dressing, with an absorbent core. The absorbent core typically comprises a polymeric foam, a fibrous hydrophilic polymeric material, a hydrogel, a matrix containing hydrocolloids, or combinations thereof. Dressings of this kind promote wound healing by providing a moist environment, while simultaneously removing excess of exudate and debris from the wound bed. Further, they serve as a barrier to protect the wound from outer contaminants and secondary bacterial colonization.

A drawback with certain materials employed as absorbent core is that when they are placed in direct contact with the wound for prolonged time, they may tend to develop adherence to the wound bed. This adherence is considered detrimental, since it usually leads to pain and damage of the newly formed wound tissue during dressing removal, eventually delaying healing. In order to minimize adherence, the use of low-adherent (or non-adherent) layers is a common practice. The low adherence refers to the adherence of the layer to the wound surface (not to the healthy skin). The low-adherent layer is sometimes present secured to the side of the dressing intended to lay proximal to the wound. Alternatively, a separated non-adherent layer component can be firstly positioned over the wound before the occlusive wound dressing comprising the absorbent core is applied. In both cases, the low-adherent layer advantageously contains openings to permit transport of wound fluid therethrough and into the absorbent core. The materials commonly described as low-adherent layers are for instance polymer films or fabrics (woven or non-woven), usually treated in a way to render them less adherent to the wound. Commercial products comprising non-adherent or low-adherent layers are e.g. Profore™ WCL (sold by Smith&Nephew), Mepitel® (sold by Mölnlycke Health Care).

With the aim of facilitating the application of the dressing to the wound site, and to hold them in position during use, the dressings often comprise an adhesive layer. The adhesive layer may be configured to cover the side of the wound dressing intended to lie over the wound during use. In this case, the adhesive layer favorably contains openings to permit passage of wound fluid from the wound bed into the absorbent core. The type of skin adhesive is suitably selected to have low-adherence to the wound, e.g. by selecting it to be hydrophobic, and thus making the use of additional low-adherent layers superfluous. U.S. Pat. No. 4,995,382 and EP 0 855 921 describe examples of such dressings. Alternatively, the adhesive layer can be configured to only contact the peri-wound skin of the wearer during use, and not the wound surface. In dressing constructions often referred as island dressings, the water-impervious backing layer extends beyond the edges of the absorbent core, and the adhesive layer is coated to the peripheral portion (border) of the backing layer, on the side intended to lie proximal to the healthy skin during dressing wearing. Such dressings are described e.g. in EP 1 303 239 and US 2009/124950. A low-adherent layer is sometimes advantageous in island dressings, as shown e.g. by the examples disclosed in U.S. Pat. No. 6,019,996.

The treatment of infected wounds, or wounds under risk of becoming infected, with non-woven or woven fabric dressings comprising an agent having some effect against microbial colonization is also known in the art. An infected wound is to be understood herein as a wound which has been entered and colonized by pathogenic microorganism like bacteria, fungi, protozoa and viruses. The non-woven or woven fabrics are usually made of natural or artificial fiber materials, or mixtures thereof, like e.g. cotton, cellulose and its derivatives, polyester, polypropylene or nylon. These wound dressings base their effect against microbial colonization in different mechanisms of action, depending on the fabric treatment. U.S. Pat. No. 4,617,326 describes a bacteria adsorbing composition comprising a woven or non-woven hydrophilic fabric, such as cotton fabric, which is treated chemically with a compound containing hydrophobic groups like dialkyl-carbamoyl chloride (DACC), especially dioctadecyl-carbamoyl chloride and dihexadecyl-carbamoyl chloride. It is proposed that when this product is applied to an infected wound, the microorganisms become bonded through hydrophobic interaction to the treated fabric and are eventually removed from the wound when the dressing is changed. Products of this kind are commercially available under the Cutimed® Sorbact (BSN medical) trademark. Alternatively, wound dressings of this kind can comprise an antimicrobial agent releasably or non-releasably incorporated into the fibers of the woven or non-woven fabric. The antimicrobial agent kills the microorganisms and/or inhibits the growth upon contact, either in the wound bed, in the exudate or inside the dressing. Some examples are contained in EP 2 253 336, WO 2007/120608, U.S. Pat. No. 6,087,549, WO 2006/121 935 and US 2002/177828. A large variety of efficient antimicrobial agents have been described in the art for this purpose, including biguanide salts like polyhexamethylbiguanide (PHMB), silver based compounds and quaternary ammonium salts, to name some.

The woven or non-woven fabric dressings with effect against microbial colonization are preferably directly applied to the wound in the form of a flat sheet, a pad, a ribbon or as several folded layers. The dressings should advantageously possess a reduced tendency to develop adherence to the wound bed. Due to their limited absorption capacity, often a secondary wound dressing comprising an absorbent core needs to be applied over the fabric material, in order to cope with the excess of wound exudate passing through it. Unitary multilayer laminate dressings are also known which combine in one article the woven or non-woven fabric layer with effect against microbial colonization, an absorbent core and optionally a water-impervious vapor-permeable backing membrane. Examples are described e.g. in U.S. Pat. No. 7,576,256 and US 2008/114279. In this prior art, the non-woven or woven fabric layer is non-detachably bonded to the absorbent core, to its surface which is proximal to the wound when the dressing is worn.

The non-woven or woven fabrics having effect against microbial colonization are ideally liquid permeable, low adherent and pliable. Disadvantageously, most of these fabrics are not significantly stretchable or expandable both in their length and width directions, corresponding to machine direction and cross direction during manufacture, showing practically absence of elasticity. As a consequence, when this fabric layer is bonded to the side of the absorbent core intended to lie proximal to the wound in a unitary dressing, at least the following drawbacks arise: a) most materials forming the absorption core, like e.g. hydrophilic foams, need to swell and expand to reach their maximum absorption capacity. When the fabric layer with reduced expansion capacity is bonded to the surface of the absorbent core, this causes the swelling of the absorbent core to be significantly restricted and its absorption capacity reduced; b) swelling of the absorbing core having bonded to its wound surface the fabric layer during absorption produces deformation and curling of the wound dressing, creating paths for wound contamination and cross-infection by external agents, and in the worst cases, leading to partial lost of contact between the dressing and the wound bed; and c) when an adhesive or a bonding layer is used to bond the fabric to the absorbent core, this layer is a source of additional costs and manufacturing complexity. Furthermore, the adhesive layer at least partially obstructs the fluid transport from the wound into the absorbent core, having a detrimental effect in the wicking capacity of wound fluids by the dressing.

From the above it is obvious that there is a need for an improved wound dressing which does not suffer from the drawbacks of the dressings known in the art, which is construed as an unitary dressing comprising an absorbent core and a non-woven or woven fabric on the wound proximal side of the absorbent core intended to lie proximal to the wound during use, and where the fabric comprises an agent having an effect against pathogenic microbial colonization of the wound.

SUMMARY OF THE INVENTION

The present invention is directed to an improved wound dressing for the treatment of skin wounds comprising a non-woven or woven fabric layer for contacting the wound and an absorbent core, where the non-woven or woven fabric layer comprises an agent having an effect against pathogenic microbial colonization of the wound, and where the non-woven or woven fabric layer is not bonded to the absorbent core. Preferably, the wound dressing is an island dressing additionally including a water-impervious vapor-permeable backing layer on its side distal to the wound when the dressing is worn, a carrier layer, and a skin adherent facing layer for securing the dressing in place in its peripheral area. By its construction, the inventive dressings have improved properties and overcome the drawbacks of the dressings known in the art, while still being straightforwardly and economically manufactured.

In accordance with a first embodiment, a wound dressing includes a vapor-permeable backing layer defining proximal and distal surfaces, and a center portion and a border portion. The words proximal and distal are used herein to refer to the position of the surface in relation to the wearer when the dressing is worn. An absorbent core is also provided which has distal and proximal surfaces. The distal surface of the absorbent core is secured to the proximal surface of the backing layer generally within the boundaries of the center portion of the backing layer. A fabric layer treated to have an effect against pathogenic microbial colonization of a wound is included having distal and proximal surfaces, and a center portion and a border portion. The fabric layer extends through both the perimeter of the absorbent core and the border portion of the backing layer, wherein its distal surface is only secured to the border portion of the proximal surface of the backing layer. The fabric layer is generally non-adherent to skin. Additionally, a carrier layer is incorporated having distal and proximal surfaces and defining an opening that generally corresponds with the center portion of the backing layer and the center portion of the fabric layer. The distal surface of the carrier layer is secured to the proximal surface of the border portion of the fabric layer. A skin adherent facing layer is applied to the surface of the carrier layer.

In a second embodiment, a wound dressing includes the elements described above in reference to the first embodiment, but with the difference that the treated fabric layer extends through the perimeter of the absorbent core and only a part of the border portion of the backing layer. In this case, the proximal surface of the part of the border portion of the backing layer which is not covered by the fabric layer is additionally secured to a part of the distal surface of the carrier layer.

In a third embodiment of the wound dressing, the skin adherent facing layer comprises a crosslinked silicone gel adhesive.

According to a forth embodiment, the treatment of the fabric layer of the embodiments above makes it at least partially hydrophobic and capable of binding pathogenic microorganisms.

In a fifth embodiment, the fabric layer of the described embodiments is treated chemically with a dialkyl-carbamoyl chloride (DACC).

In a sixth embodiment, the fabric layer of the first three embodiments is treated to carry an antimicrobial agent which is releasably or non-releasably incorporated to the fibers.

The invention in this application relates also to a wound dressing for the treatment of skin wounds with some level of exudate, and which are colonized or under risk of getting colonized by pathogenic microbes.

Further embodiments will be evident from the description of the invention and from the patent claims.

DETAILED DESCRIPTION OF VARIOUS EMBODIMENTS

A. Overview

Figure 1:
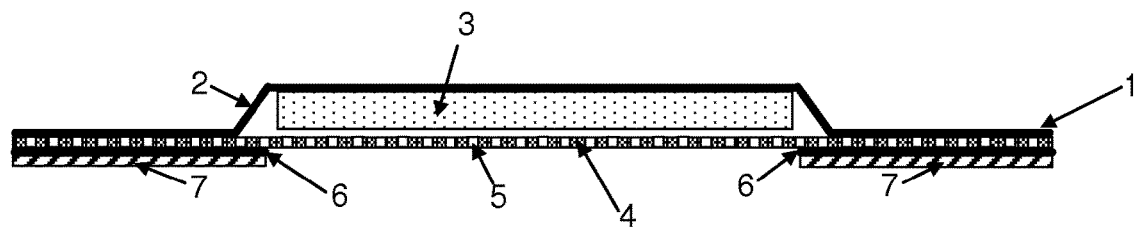
FIG. 1 is a sectional view of a first embodiment of a wound dressing according to the invention.

The embodiments of the invention can be used to handle wound exudate, to fight pathogenic microbial colonization, wound cleanse, relieve pain, combat odor and maintain a moist environment at a wound surface. The various embodiments are particularly capable of absorbing wound exudate and fighting wound infection. Different wound types with varied etiology can be dressed and treated with the different embodiments. The inventive dressings are conformable and can be designed to accommodate to different types and sizes of wounds and to various body locations. Furthermore, the adhesive properties of the skin adherent facing layer can be fitted to the intended application while taking into consideration the potential of the adhesive to cause sensitivity, allergenic reactions and to produce pain and trauma to the skin during dressing removal.

The inventive dressings may be used alone or in combination with other wound dressing or bandages known in the art to treat a wound. For instance, the embodiments of the invention can be used as secondary dressings over a primary wound dressing (like a wound filler) applied to the wound.

A better understanding of different embodiments of the invention may be had from the following description read in conjunction with the accompanying drawings in which like reference characters refer to like elements.

While the disclosure is susceptible to various modifications and alternative constructions, certain illustrative embodiments thereof are shown in the drawings and will be described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure and defined by the appended claims.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U. S. C. [section] 112, paragraph 6.

B. Environment and Context of Embodiments

Various embodiments of the invention are provided to variously be used to absorb exudate, combat odor and infection, relieve pain, wound cleanse and maintain a moist environment at a wound surface to facilitate healing of the wound. The embodiments of the invention are particularly configured for those wounds which are infected or under risk of being infected and may therefore be suitable for application for a variety of different wound types.

The various embodiments are conformable to a variety of locations on a living body, and may be dimensioned to accommodate different types and sizes of wounds. Moreover, the adhesive properties may be modified according to the location and type of wound to be treated while taking into consideration the potential for the dressing to cause sensitivity reactions, the ease of application and removal including the production of pain and trauma to wound surfaces, and the interval between wound dressing changes.

Thus, it is to be clearly understood that the various embodiments of the wound dressing according to invention may be made in any desired sizes and shapes for use over any afflicted portion of a human or other living body.

C. Various Embodiments of the Wound Dressing

As shown in FIG. 1, an embodiment of a wound dressing 1 includes a liquid impervious vapor-permeable backing layer 2 having proximal and distal surfaces. The backing layer defines a center portion and a border portion surrounding the center portion. The distal surface of an absorbent core 3 is secured to the proximal surface of the center portion of the backing layer. A treated fabric layer 4 having a series of distributed apertures 5 is included, having distal and proximal surfaces, and a center portion and a border portion. The fabric layer 4 extends through the whole perimeter defined by the absorbent core 3 and the border portion of the backing layer 2, wherein the distal surface of the fabric layer 4 is only secured to the border portion of the proximal surface of the backing layer 2. A carrier layer 6 is provided which has as well proximal and distal surfaces, wherein the distal surface of the carrier layer 6 is secured to the border portion of the proximal surface of the fabric layer 4. The carrier layer 6 defines an opening corresponding to the center portion of the backing layer 2 and which surrounds the absorbent core 3. However, in variations of this embodiment, the opening in the carrier layer 6 can also be configured not to completely correspond to the perimeter of the absorbing core, e.g. by being smaller and/or with a different shape than the absorbent core 3. Also, more than one opening can be present in the carrier layer 6. A skin adherent facing layer 7 is secured to the proximal side of the carrier layer 6.

Figure 2:
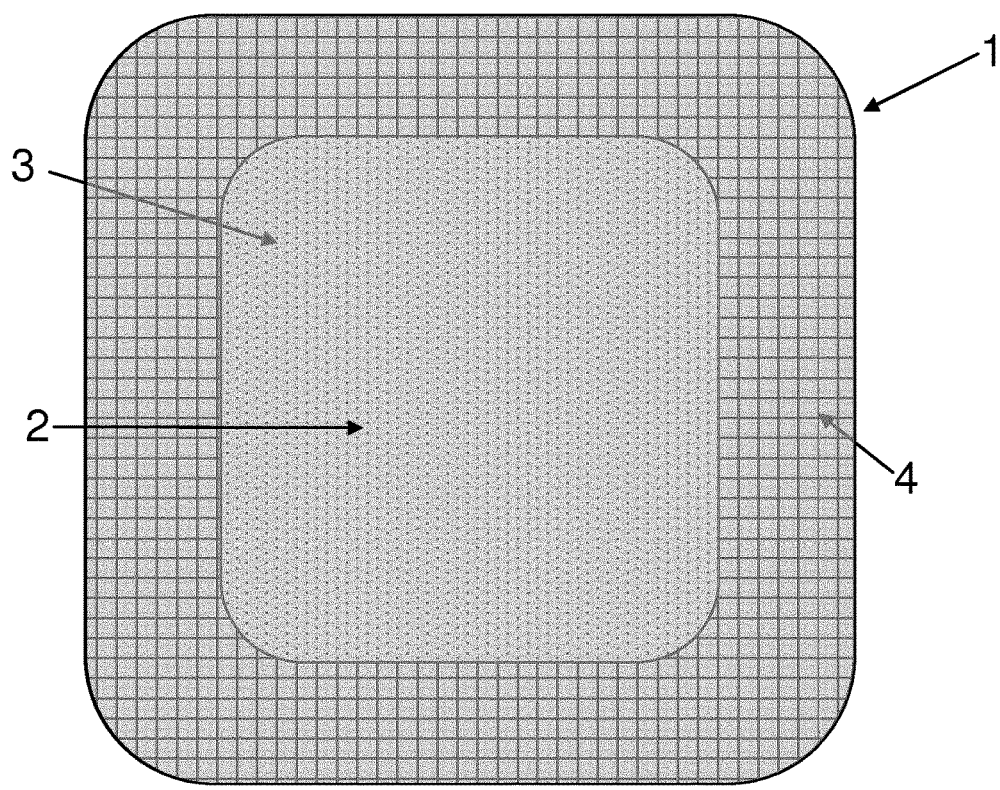
FIG. 2 is a top view of the embodiment of a wound dressing according to FIG. 1.

FIG. 2 shows a top view of the wound dressing 1 of FIG. 1. The backing layer 2 is preferably translucent, at least to a degree to permit visualization of the amount of fluid absorbed by the absorbent core 3 and its level of saturation. The shape of the dressing in this embodiment is selected to be rectangular with rounded edges. Variations of this embodiment with different shapes to adapt to various body forms, including different profiles, are possible and also inside the scope of this invention.

In the embodiments shown in FIGS. 1 and 2, the backing layer 2 is thermally bonded to the fabric layer 4, and at least portions of the backing layer 2 are secured to the distal surface of the absorbent core 3. The distal surface of the carrier layer 6 is similarly thermally bonded to the proximal surface of the fabric layer 4. Although thermal bonding is preferred, the backing layer 2 may be secured to the fabric layer 4 and the absorbent core 3 in any manner known to one skilled in the art. Such other methods include the use of adhesives, pressure molding, or ultrasonic welding. If adhesives are used for this purpose, it is preferred that these are applied as a porous layer in order to permit a high rate of water vapor transmission through it.

Figure 3:
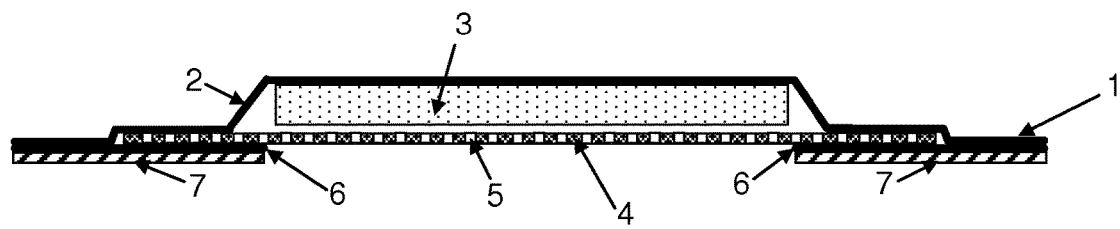
FIG. 3 is a sectional view of a second embodiment of a wound dressing according to the invention.
Figure 4:
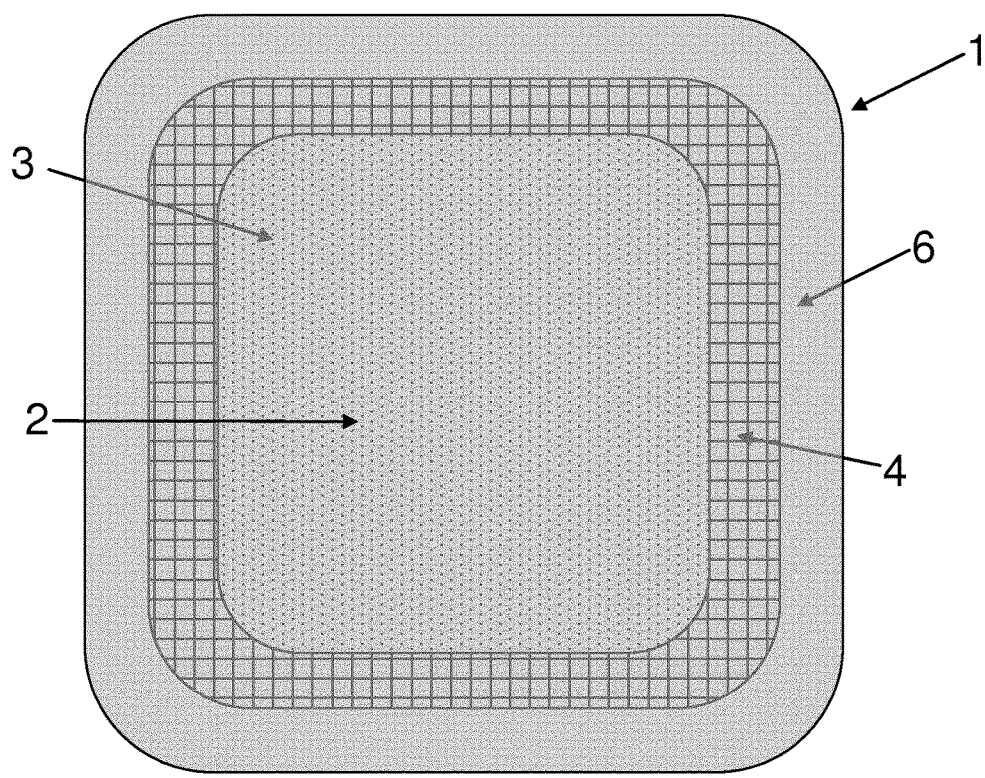
FIG. 4 is a top view of the embodiment of a wound dressing according to FIG. 3.

FIG. 3 and FIG. 4 illustrate variations of the wound dressing embodiment of FIGS. 1 and 2, in which the fabric layer 4 now has a shape that is smaller than the area of the backing layer 2 and larger than the perimeter of the absorbent core 3. The fabric layer 4 is secured with its distal surface to a part of the border portion of the proximal surface of the backing layer 2, and with its proximal surface to a part of the border portion of the distal surface of the carrier layer 6. In this embodiment, in comparison with the embodiments in FIGS. 1 and 2, a part of the proximal surface of the border portion of the backing layer 2 is directly bonded to a part of the distal surface of the carrier layer 6 extending out from the perimeter of the fabric layer 4. This embodiment is preferred in the cases where the lamination of the backing layer 2 and the carrier layer 6 to the fabric layer 4 is not sufficiently strong, or if the additional sealing achieved by securing directly the backing layer 2 with the carrier layer 6 is desired. Although the shape of the fabric layer 4 in the embodiment of FIGS. 3 and 4 is drawn to correspond to the shape of the backing layer 2, any other shape can be selected. As in the embodiments of FIGS. 1 and 2, a skin adherent facing layer 7 is secured to the proximal side of the carrier layer 6. The adherent facing layer 7 is preferably comprised of a crosslinked silicone gel adhesive.

Figure 5:
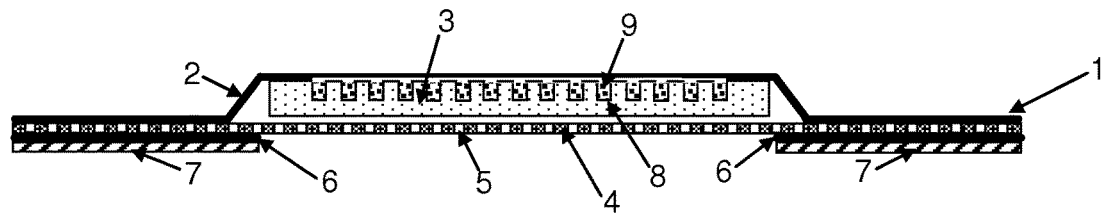
FIG. 5 is a sectional view of an embodiment of a wound dressing according to the invention, with superabsorber particles contained in receptacles formed in the distal surface of the absorbent core.

Another preferred embodiment of the present invention is shown in FIG. 5. In addition to the components of the embodiments in FIG. 1-4, the wound dressing of FIG. 5 contains a series of receptacles 8 created in the distal surface of the absorbent core 3. The receptacles 8 are filled with particles of a superabsorber material 9. In a favorable construction, portions of the backing layer 2 located at a boundary region near or at the peripheral edges of the distal surface of the absorbent core 3 can be more firmly secured to the absorbent core 3 than portions located in the center portion of the distal surface of the absorbent core 3. In this configuration, the backing layer 2 can detach from the center portion of the absorbent core 3 during absorption of wound fluid without causing complete delamination. This allows the superabsorber material contained in the receptacles to expand and use its full absorption capacity.

Figure 6:
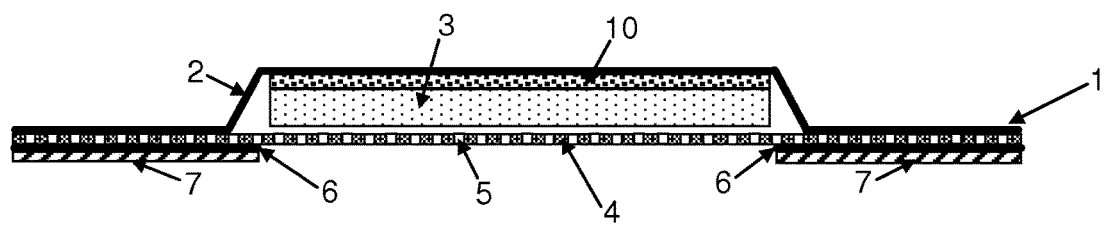
FIG. 6 is a sectional view of an embodiment of a wound dressing according to the invention, where the absorbent core is supplemented by an additional retention layer containing superabsorbers, and which is placed over the distal surface of the absorbent core.

FIG. 6 illustrates another variation of the embodiments of the invention, in which an additional retention layer 10 is located between the absorbent core 3 and the backing layer 2. The retention layer 10 may for instance comprise a fluid wicking fibrous material loaded with a superabsorber material. An alternative retention layer may comprise hydrophilic polyurethane foam loaded with superabsorbent material. The retention layer 10 enhances the absorption capacity of the absorbent core 3 by holding wound fluid absorbed and retained by the superabsorber material.

In an alternative embodiment, not shown in the figures, the adherent facing layer 7 of the previous embodiments is arranged directly on the proximal surface of the border portion of the fabric layer 4. This configuration can be used e.g. when the lamination of the backing layer 2 to the fabric layer 4 in the border portion thereof is sufficient to avoid delamination of the dressing during use.

Figure 7:
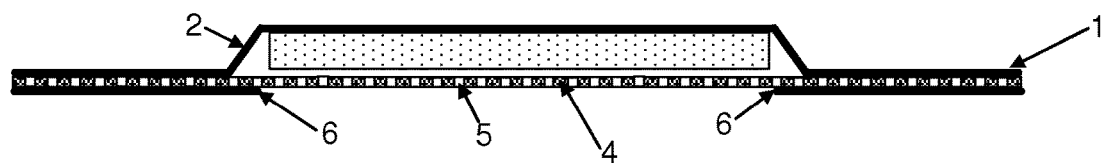
FIG. 7 is a sectional view of another embodiment of a wound dressing according to the invention, where no skin adherent facing layer is present.

In the embodiment shown in FIG. 7, the wound dressing of the first embodiment is modified not to include the skin adherent facing layer 7. This embodiment is preferred when the adhesive property of the wound dressing is detrimental or not required.

Although not shown, a release paper or film is optionally applied to the proximal surface of the skin adherent facing layer, and preferably covering the whole proximal surface of the wound dressing, on any of the embodiments of this invention. The release paper or film is removed and discarded before the dressing is used.

In the various embodiments described herein, the backing layer 2 preferably comprises a thin polymeric elastic and flexible film, particularly an elastomer film. The backing layer advantageously serves as bacterial barrier, while still being permeable to water vapor. The backing film is continuous and free of macroscopic pores extending through its thickness. Films of this type are known, for example polyurethane films, through which water vapor can diffuse. Thin high density foam membranes, consisting predominantly of closed cells, can be alternatively used as the backing layer. The polyurethane films useful as backing layers are commercially available e.g. from Exopack Advanced Coatings (Matthews, N.C.), under the product designation INSPIRE. Polyurethane films exhibiting resilient properties that allow the film to have good conformability and high degree of stretchability are preferred.

The backing layer alone may have suitably a moisture vapor transmission rate (MVTR) of 500 to 14600 $g/m^2/24$ hrs, preferably from 1000 to 2700 $g/m^2/24$ hrs. at 37° C., if measured according to DIN EN 13726-2. Higher MVTR values can be advantageous in order to delay the saturation point of the wound dressing in strongly secreting wounds. Low MVTR values can be beneficial in assuring a moist micro-environment around the wound in the case of low-secretion wounds. The thickness of the backing layer is preferably in the range of 10 to 60 micrometers, more preferably about 25 micrometers. The backing layer can be transparent to allow the level of filling or moisture in the wound dressing or the status of the wound to be assessed without having to remove the dressing. The backing layer can be filled with colouring agents. In general the film has a thickness of 10-500 μm and typically 15 to 45 μm, whereby film thicknesses of 30+/−5 micrometers are used in particular.

The absorbent core 3 of the embodiments of the invention may be selected from a variety of different materials known within the art of wound dressings, or combinations of them, and they may be arranged in different ways. In addition to absorption, an effective wicking mechanism is desirable to rapidly direct fluids away from the proximal surface of the absorbent core to more remote areas (i.e., the receptacles containing the discrete portions of superabsorbent material in the embodiment of FIG. 5, or the retention layer of the embodiment of FIG. 6).

The preferred material for the absorbent core comprises a flexible conformable open-cell foam that is at least slightly hydrophilic. The pore size is uncritical with respect to the other layers; suitable foams have an open cell size of 30-700 micrometers, and preferably a cell size of 50 to 300 micrometers. The absorbent foam may also comprise a gradient of cell sizes across the thickness of the absorbent core. The open cells permit transport of fluid and cellular debris into and within the foam. The absorption capacity with free swelling of the foams applicable in the invention ranges from 5 g/g to 50 g/g if measured according to DIN EN 13726-1 section 3.2, preferably from 10 g/g to 20 g/g. The absorbent core may expand about 60-300% its volume when saturated with fluid. It is evident that non-hydrophilic foams may used as well, where the required absorption is achieved e.g. by capillary action and/or by the incorporation of hydrophilic particles in the foam.

The foam may be made, for example, of polyurethane, cellulose, carboxylated butadiene-styrene rubber, polyester foams, hydrophilic epoxy or polyacrylate. In a preferred embodiment, the foam is formed from hydrophilic polyether polyurethane, such as the polyurethane foam made by Polymer Health Technologies (Ebbw Vale, UK) under product designation 1012.

The thickness of the absorbent core may range from 0.5 mm to 20 mm, and is preferably between 2 mm and 5 mm.

It will be understood that the absorbent core is not limited to being constituted of foam. In an alternative embodiment, the absorbent core may be a hydrophilic porous woven or non-woven fabric material produced by a number of means using known materials available to those skilled in the art.

For example, the absorbent core may exist as a bulky, loosely formed web composed of very short cellulosic fibers arranged in a random or non-random array, a pad of cellulose flakes, chitosan flakes, or a polymeric fibril matrix, as well as a mixture thereof.

The absorbent core may include an array of receptacles formed therein, as exemplified in the preferred embodiment depicted in FIG. 5. The receptacles are distributed in the distal side of the absorbent core and may be defined in any suitable preselected pattern. The receptacles may contain a desired bulk or quantity of discrete portions of superabsorbent material. Preferably, such receptacles have an uniform shape and size and extend at least partially across the distal surface of the absorbent core. The pattern of receptacles may be tailored to include a higher concentration of those at specific regions of the dressing as opposed to other regions.

The superabsorbent material used in the embodiments of the invention is preferably comprised of superabsorbent polymeric granulates, flakes or powders that swell on exposure to water and form a hydrated gel (hydrogel) by absorbing large amounts of water. Superabsorbents are defined herein as materials that exhibit the ability to absorb large quantities of liquid, i.e. in excess of 10 to 15 parts of liquid per part thereof. Superabsorber materials usually employed in the field of wound dressings are starch graft copolymers, cross-linked carboxymethylcellulose synthetic or natural derivatives and modified hydrophilic polyacrylates. Preferably, the superabsorbent material used in the dressing of the present invention is composed of particles of cross-linked polyacrylic-acid and the salts thereof.

Superabsorbent particles are available commercially, for example starch graft polyacrylate hydrogel powders are available from Hoechst-Celanese (Portsmouth, Va.). Other crosslinked sodium polyacrylate superabsorbent particles are marketed under the trademark FAVOR (Degussa AG, Germany). The superabsorbent particles are preferably in the form of granules or flakes with large surface area. The size of the particles is typically within the range of 10 to 1000 micrometers when dry. Preferably, the particle size of the absorbent particles ranges from 100 to 900 micrometers. Preferably, the particles are insoluble in the wound exudate.

According to a further embodiment of the wound dressing of the invention, the absorbent core 3 may include a plurality of discrete portions of superabsorbent material incorporated therein. The discrete portions of superabsorbent particles may be granulates, flakes or powders that are enmeshed or freely disposed in pores or free spaces of the absorbent core. Alternatively, the superabsorbent material may be homogenously distributed in the absorbent core and attached to it. In an embodiment, the absorbent core comprises hydrophilic polyurethane foam, where a superabsorber material is mixed with any of the components of the foam previous to foaming, so as to obtain a foam material with the superabsorber material homogenously distributed therein and substantially anchored to the foam.

FIG. 6 illustrates another embodiment of the invention, where an additional retention layer 10 is placed between the absorbent core 3 and the backing layer 2. The proximal surface of the retention layer may be attached to the distal surface of the absorbent core in at least portions thereof. The attachment can be effected by any method known, like thermal bonding, ultrasound welding or by using an adhesive, and the transport of fluid from the absorbent core to the retention layer should not be prevented therewith. The distal surface of the retention layer is thermally bonded to the backing layer in at least portions thereof. The retention layer preferably comprises superabsorbent material distributed homogenously in a wicking material matrix. The wicking material matrix can be formed by foam, woven or non-woven web. These materials are well known as wicking layers to those skilled in the art of wound dressings. In a preferred embodiment, the retention layer is elastomeric and pliable, and comprises a wicking material formed from a hydrophilic non-woven meltblown polyurethane containing superabsorber particles incorporated into its structure. Materials of this kind are know and exemplified in e.g. U.S. Pat. No. 4,957,795. This embodiment permits the combination of the fast wicking and fluid transport properties of an absorbent core in proximity to the wound surface, with the high absorption and retention properties of the superabsorber in the retention layer in a region distanced from the wound.

The carrier layer 6 comprised in the embodiments of the invention serves to provide additional security against dressing delamination during wearing, and to carry the skin adherent facing layer, in the cases where this latter layer is present. Preferably, the carrier layer reinforces the border portion of the backing layer and fabric layer, thus increasing the stiffness of this part of the dressing and making the dressing application easier. The preferred carrier layer is a thermoplastic film that can be thermally bonded to the fabric layer. An example of such a film is manufactured by Epurex Films under the product designation Platilon. Alternatively, other films, foams and mesh materials may be employed that can be thermally bonded to the fabric layer, or secured to the fabric layer by other methods known in the art, including the use of adhesives, stitching, pins or ultrasound welding. The thickness of the carrier layer is suitably from 10 micrometer to 150 micrometers, and preferably from 20 micrometers to 60 micrometers. Carrier layers which are porous, perforated or with a sufficient moisture vapor transmission rate (MVTR) are preferred in order not to obstruct the skin breathability. Suitable carrier layers are continuous conformable films having a MVTR of 300 to 10000 $g/m^2/24$ hrs, preferably from 500-1500 $g/m^2/24$ hrs at 37° C. if measured according to DIN EN 13726-2.

The embodiments of this invention comprise a fabric layer 4 of a woven or non-woven material which comprises an agent having an effect against a pathogenic microbial colonization of a wound. This layer is intended to lie in direct contact with the wound when the dressing is worn. The fabric layer is generally non-adherent to the skin. It is also preferred that this layer develops low or non-adherence to the wound bed during wearing, in order to minimize pain and damage to newly created healing tissue during dressing removal. The woven or non-woven fabric may be sufficiently permeable or have a series of apertures in order to permit the passage of wound fluid from the wound surface into the absorbent core. The apertures may be those naturally occurring in the fabric or they may be perforations. Suitable fabric layers are flexible and pliable. The thickness of the fabric layer may range from 10 micrometers to 2 millimeter, preferably from 50 micrometers to 500 micrometers.

In a preferred embodiment, the fabric layer comprises a cellulose acetate textile or a cotton textile which has been treated chemically with a strongly hydrophobic material like dialkyl-carbamoyl chloride (DACC), specifically dioctadecyl-carbamoyl chloride and dihexadecyl-carbamoyl chloride, according to the methods described in U.S. Pat. No. 4,617,326. By this treatment, the DACC is non-releasably covalently bonded to the textile material and gives the fabric a strong hydrophobic characteristic. It is proposed that when this treated fabric layer gets in contact with pathogenic microorganisms present in the wound or contained in the wound exudate, the microorganisms are bonded to the fibers of the fabric through hydrophobic interaction, eventually limiting the capacity of the microorganisms to spread and reproduce. The microorganisms adhered to the treated fabric are then removed from the wound during dressing change. This fabric layer is low-adherent, pliable and conformable, and substantially non-expandable and inelastic. Fabric layers of this kind are described in U.S. Pat. No. 4,617,326 and U.S. Pat. No. 7,576,256 and are commercially available i.e. from BSN medical under the trademark Cutimed® Sorbact.

It will be evident that other woven or non-woven fabric layers may be used without departing from the scope of the invention. Woven or non-wovens fabrics which have been treated to carry one or several antimicrobial agents are known and many variations thereof are described in the patent and scientific literature. The antimicrobial agents can be releasably or non-releasably bonded to the fabric substrate. By releasably bonded it is meant that the incorporated antimicrobial agent is released into the wound in certain concentration during wearing, often by dissolution and migration in the wound exudate. Usually, the fabric is a woven or non-woven, gauze or knitted fabric, made of polymeric fibers of natural or synthetic origin, like cotton or rayon. Various antimicrobial agents and combinations thereof are applicable, including copper, silver and silver salts such as silver sulphadiazine, iodine sources such as povidone-iodine, chlorhexidine or a salt thereof, polyhexamethylene biguanide (PHMB) or a salt thereof or quaternary ammonium salts. Some exemplary commercially available fabric dressings comprising treated fabric layers of this kind are Kerlix™ AMD from Covidien, Silverlon® from Argentum Medical or Nimbus® from Quick-Med Technologies.

The antimicrobial agents can be contained in the fabric layer in a way that a release of a controlled concentration of this agent to the wound during time is achieved. This can be done e.g. by incorporating the antimicrobial agent in a resorbable polymer matrix, such as collagen or polylactic acid. As the polymer matrix comes in contact with body fluids and it is biodegraded, the antimicrobial agent is released. The resorbable polymer matrix can be present in the fabric as discrete particles or fibers. Alternatively, fibers of metals like copper or silver, including microfibers and nanofibers, may be contained in the fabric layer, alone or mixed with other fibers. In contact with body fluids, the metal fibers slowly dissolve releasing the ionic metal species which are active as antimicrobial agents.

Other medicaments, which have a beneficial effect for the wound treatment and wound healing, may be incorporated into the fabric layer without departing from the scope of the invention. Medicaments of this type are known in the art and not limited in this invention, and include for example hemostatic agents, anti-inflammatories, analgesics, growth factors, protease inactivators, proteins, enzymes and nucleic acids.

Since the—treated—woven or non-woven is not bonded to the absorbent core, woven or non-wovens can be selected out of a great number such fabrics having different pharmaceutically active agents. Thus, it is possible to design wound dressing according to the desired therapeutic activity or activities. Another great advantage of the fact that the woven or non-woven fabric layer is not directly or indirectly connected to the absorbent core, is that the latter can swell and expand to a higher degree during absorption than if the fabric layer were directly bonded to the absorbent core. In other words, the absorbent core's absorption capacity is not limited by the reduced expansion capacity of the fabric layer. Also, dressing deformations like curling during wearing are significantly reduced or eliminated. In an alternative embodiment of the invention, not depicted in the drawings, the fabric layer comprises at least one ply or at least one fold. The at least one ply or at least one fold is adapted to unfold as the wound dressing absorbs wound fluid, creating a larger room for the absorbent core to swell.

The skin adherent layer 7 contained in the embodiments of this invention may comprise various pressure sensitive adhesives to render the border portion of the wound dressing adhesive to the skin. The pressure sensitive adhesive is preferably selected to be reasonably skin compatible and hypoallergenic. The adhesive may be comprised of a polymer composition from the group consisting of acrylic copolymer, polyisobutylene, polyurethane and polymeric silicone. The skin adherent layer may also comprise two or more adhesive materials in a stacked arrangement, or may be different adhesive materials arranged in alternating parallel strips to one another.

The adhesion power to skin of the skin adherent layer is selected to be enough to hold the dressing in place for sufficient time, but avoiding causing excessive pain to the wearer or damage of the sensitive skin surrounding the wound. Low trauma adhesives are preferred which are known in the art of wound dressings, like e.g. soft gels or low tack adhesives based on crosslinked polyurethane, crosslinked silicone or acrylic gels. The adhesion power of the skin adherent layer can be evaluated by measuring the force required to peel a sample comprising the adhesive from a stainless steel plate. The methods for measuring the peeling strength are various and well known to those in the art of adhesive tapes and bandages. In order to obtain a better evaluation of the adhesion power of the skin adherent layer, the peeling experiments can be done using the back or forearm skin of volunteers instead of stainless steel plates.

The hydrophobicity and hydrophilicity of the adhesive can be chosen to fit the intended application. Thus, a hydrophilic tacky hydrogel or a relatively hydrophobic adhesive mass loaded with hydrocolloid material may be chosen to form the skin adherent layer. These materials have the advantage of being able to absorb aqueous fluid to some extend and in some cases to stick well to wet surfaces. For other applications, a hydrophobic silicone pressure sensitive adhesive or a silicone elastomer as those known in the art may be appropriate. In general, hydrophobic skin adherent layers have the advantage of not sticking to the wet wound surface or to moist sensitive periwound skin.

Preferably, the skin adherent layer is a tacky silicone gel coated onto the carrier layer. The silicone gel comprises an elastomeric crosslinked polydimethylsiloxane, which has been hardened by any curing reaction known for this kind of polymeric systems, like addition curing or condensation curing. The preferred curing reaction is however addition (also known as hydrosilylation curing), where the silicone gel precursors containing vinyl and hydride functionalities in defined ratio are crosslinked and hardened at room temperature or higher temperatures in the presence of a platinum catalyst. Commercial tacky silicone gels are commonly provided as two components which need to be mixed in a certain ratio in order to start the curing reaction. Examples of commercially available silicone gels are those from NuSil Technology (Carpenteria, Calif.) like MED-6340 or MED-6345, or those from Wacker Chemie AG (Munich, Germany) like Silpuran2130.

The skin adherent facing layer comprising a silicone gel is coated to the proximal surface of the carrier layer by any conventional method known in the art. The coating weight of the adhesive is preferably from 20 g/m$^2$ to 300 g/m$^2$, more preferably from 80 g/m² to 150 g/m². In order to improve the anchoring of the silicone gel to the carrier layer, the surface of the carrier layer can be treated e.g. with a primer agent or by corona treatment. In an alternative embodiment, the carrier layer may be selected having an rough proximal surface, or the carrier layer may be chosen to comprise a two-ply material of two plastic layers, where the layer contacting the silicone gel has a rough proximal surface.

While the skin adherent layer is shown in FIGS. 1, 3, 5 and 6 to be continuous, it may be configured to include a plurality of apertures or perforations in a pattern. The coating may as well be selected to be microporous or macroporous. The apertured configuration of the coating offers the benefit of permitting a higher rate of moisture transport through the skin adherent facing layer.

Numerous methods may be adequate to manufacture the embodiments of the wound dressing described herein. Suitable steps have been described e.g. in U.S. Pat. No. 7,396,975. Of course, the corresponding modifications and additional steps need to be undertaken in order to incorporate the treated fabric layer to the wound dressing.

According to one exemplary method of manufacture for the embodiments showed in FIGS. 1 and 2, the process comprises a series of consecutive steps. It starts the step of providing a carrier layer having removable paper liner thereon dispensed from a roll. The carrier layer is transported and a surface treatment substance or primer dissolved in a solvent is applied on a proximal surface of the carrier layer. The solvent accompanying the primer is allowed to evaporate prior to the next step. Suitable primers include silicone primers, such as those commercially available and known in the art.

Next, a layer of uncured silicone gel is homogenously extruded onto the primer treated proximal surface of the carrier layer. The carrier layer with the uncured silicone gel layer is transported over a heated drum and maintained there until the silicone gel precursor is substantially fully cured. Suitable drum temperatures depend on the silicone gel used and the speed of the coating line, and usually range from 80° C. to 180° C., more preferably from 110° C. to 150° C.

After the silicone gel precursor has cured and formed the skin adherent facing layer of the embodiments of the invention, the carrier layer is removed from the drum and a die cutter is used to cut and remove the center portion from the carrier layer coated with the silicone gel. The removal of the center portion of the carrier layer effectively forms an opening through the carrier layer and the cured silicone gel layer. Subsequently, the carrier layer paper liner is removed from the distal surface of the carrier layer. A new release paper or film is applied to the proximal surface of the silicone gel layer.

The treated fabric layer is then applied from a roll, planar and extending over the distal surface of the carrier layer, also covering the opening created in its center portion.

The absorbent core is placed over the distal surface of the fabric layer, centered over the opening created in the carrier layer.

The backing layer is disposed over the distal surfaces of the absorbent core and the carrier layer. A platen is provided as having a generally planar border region and a recessed center region relative to the planar border region that generally corresponds to the shape of the absorbent core. The platen is preferably heated to an elevated temperature suitable to thermally bond the backing layer to the fabric layer, the carrier layer to the fabric layer, and to secure the absorbent core to the backing layer. This temperature of the platen may vary in different parts thereof. The platen is urged against the distal surface of the backing layer to generate pressure thereon sufficient to substantially cause thermal bonding of the backing layer to the fabric layer and to at least portions of the absorbent core, and simultaneously to cause thermal bonding of the carrier layer to the fabric layer. After a period of time sufficient to thermally bond the different layers with each other, the platen is removed from the distal surface of the backing layer.

Subsequent to the thermal bonding of the different layers, the wound dressing is cut to size with a die cutter.

After their manufacture, the wound dressings of the invention can be packaged and sterilized by any conventional method like gamma irradiation or treatment with ethylene oxide.

Accordingly, the present invention relates firstly (1.) to a unitary wound dressing comprising:
an absorbent core,
a backing layer, and
a woven or non-woven fabric layer comprising an agent having an effect against pathogenic microbial colonization of a wound,
wherein the woven or non-woven fabric layer is bonded to at least a part of the border portion to the proximal surface of the backing layer bordering the center portion,
and wherein the non-woven or woven fabric is not bonded to the absorbent core.

2. The present invention relates to a wound dressing according to 1., where the woven or non-woven fabric layer is secured to the complete part of the proximal surface of border portion of the backing layer.

3. Moreover, the present invention relates to a wound dressing according to 1. or 2., further comprising a carrier layer secured to the woven or non-woven fabric in at least a part of the border portion thereof and having at least an opening through which fluid can pass from the wound into the absorbent core.

4. Moreover, the present invention relates to a wound dressing according to 1. to 3., where the carrier layer comprises a conformable polyurethane film.

5. Moreover, the present invention relates to a wound dressing according to any of 1. to 4., where the wound dressing comprises a skin adherent facing layer disposed in the border portion of its proximal side.

6. Moreover, the present invention relates to a wound dressing according to 5., where the skin adherent facing layer comprises a silicone material, preferably a silicone gel.

7. Moreover, the present invention relates to a wound dressing according to any of any of 1. to 6., where the backing layer comprises a water-impervious vapor-permeable layer, preferably a conformable polyurethane film.

8. Moreover, the present invention relates to a wound dressing according to any of 1. to 7., where the woven or non-woven fabric layer comprising an agent having an effect against pathogenic microbial colonization of a wound comprises a cellulose acetate textile or a cotton textile which has been treated with dialkyl-carbamoyl chloride to give the fabric a strong hydrophobic characteristic.

9. Moreover, the present invention relates to a wound dressing according to any of 1. to 8., where the woven or non-woven fabric layer comprising an agent having an effect against pathogenic microbial colonization of a wound comprises a fabric layer carrying at least one antimicrobial agent selected from the group consisting of copper, silver, silver salts, iodine, povidone-iodine, chlorhexidine, chlorhexidine salts, polyhexamethylene biguanide, polyhexamethylene biguanide salts, quaternary ammonium salts and combinations thereof.

10. Moreover, the present invention relates to a wound dressing according to any of 1. to 9., where the at least one antimicrobial agent is releasably incorporated into the fabric.

11. Moreover, the present invention relates to a wound dressing according to any of 1. to 10., where the absorbent core comprises hydrophilic polyurethane foam.

12. Moreover, the present invention relates to a wound dressing according to any of 1. to 11., where the absorbent core comprises a series of receptacles created in its distal surface filled with superabsorber particles.

13. Moreover, the present invention relates to a wound dressing according to any of 1. to 12., where the absorbent core comprises a retention layer loaded with superabsorbent material.

14. Furthermore, the present invention relates to a wound dressing according to any of 1. to 13. for use in a method for treatment of a wound.

15. Furthermore, the present invention relates to process for the manufacture of a wound dressing according to 1. to 13., comprising the following steps:
a) providing a carrier layer;
b) applying a surface treatment substance or primer dissolved in a solvent on the proximal surface of the carrier layer;
c) evaporating the solvent if a primer which is dissolved in a solvent is used;
d) extruding a layer of uncured silicone gel comprising at least one silicone gel precursor homogenously onto the primer treated proximal surface of the carrier layer;
e) curing the uncured silicone gel by heating the at least one silicone gel precursor;
f) removing the center portion from the carrier layer;
g) applying the treated fabric layer over the distal surface of the carrier layer;
h) placing the absorbent core over the treated fabric layer centered over the opening created in the carrier layer;
i) disposing a backing layer over the distal surfaces of the absorbent core and the carrier layer;
j) thermal bonding of the layers.

It will be understood that the above described embodiments and methods are illustrative in nature, and that modifications thereof may occur to those skilled in the art. Accordingly, this invention is not to be regarded as limited to the embodiments disclosed herein, but is to be limited only as defined in the appended claims.

The invention claimed is:

1. A unitary wound dressing comprising:
an absorbent core defining a distal surface and a proximal surface, and further defining an outermost edge surrounding the entire absorbent core;
a backing layer defining a distal surface, a proximal surface, a center portion, and a border portion, wherein the distal surface of the absorbent core is secured to the proximal surface of the backing layer within boundaries of the center portion of the backing layer;
a woven or non-woven fabric layer defining a distal surface, a proximal surface, a center portion, and a border portion, the fabric layer extending through both a perimeter of the absorbent core and the border portion of the backing layer, the fabric layer comprising an agent having an effect against microbial colonization of a wound, wherein the woven or non-woven fabric layer is bonded to the proximal surface of at least a part of the border portion of the backing layer but is not bonded to the absorbent core; and
a carrier layer defining a distal surface and a proximal surface, the carrier layer having at least an opening through which fluid can pass from the wound into the absorbent core, the distal surface of the carrier layer being secured to at least a part of the proximal surface of the border portion of the fabric layer, wherein the at least an opening has an outermost edge that surrounds the outermost edge of the entire absorbent core when viewed from above or below.

2. The wound dressing according to claim 1, where the distal surface of the woven or non-woven fabric layer is secured to a complete part of the proximal surface of the border portion of the backing layer.

3. The wound dressing according to claim 1, where the carrier layer comprises a conformable polyurethane film.

4. The wound dressing according to claim 1, where the wound dressing comprises a skin adherent facing layer disposed in the border portion of its proximal side.

5. The wound dressing according to claim 4, where the skin adherent facing layer comprises silicone gel.

6. The wound dressing according to claim 1, where the backing layer comprises a conformable polyurethane film.

7. The wound dressing according to claim 1, where the woven or non-woven fabric layer comprising an agent having an effect against microbial colonization of a wound comprises a cellulose acetate textile or a cotton textile which has been treated with dialkyl-carbamoyl chloride.

8. The wound dressing according to claim 1, where the woven or non-woven fabric layer comprising an agent having an effect against pathogenic microbial colonization of a wound comprises a fabric layer carrying at least one antimicrobial agent selected from the group consisting of copper, silver, silver salts, iodine, povidone-iodine, chlorhexidine, chlorhexidine salts, polyhexamethylene biguanide, polyhexamethylene biguanide salts, quaternary ammonium salts and combinations thereof.

9. The wound dressing according to claim 8, where the at least one antimicrobial agent is releasably incorporated into the fabric.

10. The wound dressing according to claim 1, where the absorbent core comprises hydrophilic polyurethane foam.

11. The wound dressing according to claim 1, where the absorbent core comprises a series of receptacles created in its distal surface filled with superabsorber particles.

12. The wound dressing according to claim 1, where the absorbent core comprises a retention layer with a superabsorbent material.

13. Process for preparing a unitary wound dressing comprising:
a) applying a surface treatment substance on the proximal surface of a carrier layer, the carrier layer defining a distal surface and a proximal surface;
b) extruding a layer of uncured silicone gel homogenously onto the proximal surface of the carrier layer;
c) curing the uncured silicone gel by heating the silicone gel precursor;
d) removing a center portion from the carrier layer to provide an opening in the carrier layer;
e) applying a treated fabric layer over the distal surface of the carrier layer;
f) placing an absorbent core over the treated fabric layer centered over the opening created in the carrier layer, the absorbent core defining a distal surface and a proximal surface, and further defining an outermost edge surrounding the entire absorbent core;
g) disposing a backing layer over the distal surfaces of the absorbent core and the carrier layer; and h) thermally bonding the layers, wherein the opening in the carrier layer has an outermost edge that surrounds the outermost edge of the entire absorbent core when viewed from above or below.

14. The process of claim 13, wherein the absorbent core comprises a retention layer.

15. The process of claim 13, wherein the treated fabric layer comprises an agent having an effect against microbial colonization of a wound.

16. Process for preparing a unitary wound dressing, the process comprising:
   a) applying a primer dissolved in a solvent on the proximal surface of a carrier layer, the carrier layer defining a distal surface and a proximal surface;
   b) evaporating the solvent if a primer which is dissolved in a solvent is used;
   c) extruding a layer of uncured silicone gel homogenously onto the primer treated proximal surface of the carrier layer;
   d) curing the uncured silicone gel by heating the silicone gel precursor;
   e) removing the center portion from the carrier layer, creating an opening in the carrier layer;
   f) applying a treated fabric layer over the distal surface of the carrier layer;
   g) placing an absorbent core over the treated fabric layer centered over the opening created in the carrier layer, the absorbent core defining a distal surface and a proximal surface, and further defining an outermost edge surrounding the entire absorbent core;
   h) disposing a backing layer over the distal surfaces of the absorbent core and the carrier layer; and
   i) thermally bonding the layers, wherein the opening in the carrier layer has an outermost edge that surrounds the outermost edge of the entire absorbent core when viewed from above or below.

17. The process of claim 16, wherein the absorbent core comprises a retention layer.

18. The process of claim 16, wherein the treated fabric layer comprises an agent having an effect against microbial colonization of a wound.

* * * * *